US00PP09765P

United States Patent [19]

Utecht

[11] Patent Number: Plant 9,765

[45] Date of Patent: Dec. 24, 1996

[54] GERANIUM PLANT NAMED 'FISBRAVO'

[75] Inventor: Angelika Utecht, Montabaur, Germany

[73] Assignee: Florfis AG, Binningen, Switzerland

[21] Appl. No.: 518,897

[22] Filed: Aug. 29, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Foley & Lardner

[57] ABSTRACT

A new and distinct cultivar of geranium plant named Fisbravo, characterized by its bluish pink colored, round flowers with large purple eyes on petals, dark green foliage with weak zonation, medium plant habit and comparatively early flower response.

1 Drawing Sheet

The present invention comprises a new and distinct cultivar of geramium, botanically known as *Pelargonium zonale,* and hereinafter referred to by the cultivar name Fisbravo.

Fisbravo is a product of a planned breeding program which had the objective of creating new geramium cultivars with pink colored flowers with markings on petals, dark green foliage and well branched plant habit.

Fisbravo was originated from a hybridization made by inventor Angelika Utecht in a controlled breeding program in Hillscheid, Germany, in 1990. The female parent was the cultivar Fisbluri, disclosed in U.S. Plant Pat. No. 8,712, and characterized by mainly violet pink colored flowers with purple red eyes on the petals, medium to dark green foliage with weak zonation, and medium to vigorous growth.

The male parent of Fisbravo was an unnamed hybrid seedling derived from crossings between the commercial cultivars Purpurball (Purlapen), having double, purple colored flowers and comparatively light green foliage; Dresdner Puppe Rosa, characterized by its single pink colored flowers with purple eyes and medium green foliage; Summer Cloud, having white semi-double flowers, vigorous growth, and foliage without zonation, and Rospen, having violet-pink semi-double flowers with purple eyes, zoned foliage and compact growth.

Fisbravo was discovered and selected as one flowering plant within the progeny of the stated cross by Angelika Utecht in 1991 in a controlled environment in Galdar, Gran Canaria, Spain.

The first act of asexual reproduction of Fisbravo was accomplished when vegetative cuttings were taken from the initial selection in Jun. 1991 in a controlled environment in Galdar, Gran Canaria, Spain, by, or under the supervision of the inventor.

Horticultural examination of plants grown from these cuttings initiated in May 1992 in Hillscheid, Federal Republic of Germany, and continuing thereafter, has demonstrated that the combination of characteristics as herein disclosed for Fisbravo are firmly fixed and are retained through successive generations of asexual reproduction.

Fisbravo has not been observed under all possible environmental conditions. The phenotype may vary significantly with variations in environment such as temperature, light intensity and daylength without, however, any variation in genotype.

The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Fisbravo, which, in cobination, distinguish this geranium as a new and distinct cultivar:

1. Bluish pink main flower color, and large purple pink flares on upper and lower petals.
2. Almost round, slightly semi-double flower form.
3. Dark green foliage with weak zonation.
4. Medium height.
5. Comparatively early flower response for a dark green cultivar.

Of the many commercial cultivars known to the inventor, the most similar in comparison to Fisbravo is the parent cultivar Fisbluri. In comparison to Fisbluri, Fisbravo has a weaker bluish pink-main flower color (74 D vs. about 66 C for Fisbluri). In addition, the markings on the lower petals of Fisbravo are almost the same size as those on the upper petals, due to the nearly round flower shape. These markings are larger than those of Fisbluri, though the purple color is not quite so intense and fades near the margin. Further, Fisbravo starts flowering somewhat earlier and produces more flowers through the summer, and the plant habit of Fisbravo is more compact.

The accompanying photographic drawing is a top perspective view and shows typical flower and foliage characteristics of Fisbravo, with colors being as true as possible with illustrations of this type.

In the following description, color references are made to The Royal Horticultural Society Colour chart.

The color values were determined indoors from flowers taken from plants grown in a greenhouse in May 1994 in Hillscheid, Federal Republic of Germany.

Classification:

*Botanical.*—A hybrid of the species *Pelargonium zonale* l'Hert.

*Commercial.*—Zonal geranium, cv., Fisbravo.

Inflorescence

Umbel:

*Shape.*—Broad, flat semi-spherical.

*Average diameter.*—120 mm.

*Average depth.*—55 mm.

*Peduncle length.*—145 mm.

*Peduncle color.*—Mainly dark red.

*Pedicel length.*—28 mm.

Pedicel color.—Light to dark red.

Number of open flowers per umbel.—22.

Corolla:

*Average diameter.*—47 mm.

*Form.*—Semi-double.

*Number of petals.*—6–8.

*Number of petaloids.*—1–3.

*Color (general tonality from a distance of three meters).*—Light bluish pink petals with purple pink eyes and white bases.

*Main color of upper surface of petals, near margin.*—74 D.

*Markings on upper and lower petals.*—57 B–C.

*Color of lower surface of petals.*—Light violet pink (75 B to 73 B) or lighter, almost white; weak pink veins.

*Color of sepals.*—Medium green, dark red at the base.

*Number of sepals.*—5.

Bud:

*Shape.*—Elliptical.

*Color (adaxial).*—Green.

*Color (abaxial).*—Main color often light pink or whitish, pink near edge of petals.

Reproductive organs:

*Androecium.*—5–7 fertile anthers, white and pink filaments, orange pollen.

*Gynoecium.*—5–6 lobed stigma, dark red, pink style.

*Seed.*—No seed set observed.

Spring flowering response period: In Hillscheid, Germany, in 1994 plants of Fisbravo had on average 0.8 umbels with at least one flower opened 11 weeks after planting of unrooted cuttings.

Outdoor flower production: The flower count in 1994 in Hillscheid, Germany, indicated about 40 umbels per plant for May through Aug. observation period.

Durability: Good shatter resistance, relatively good rain resistance.

Plant

Foliage:

*Form.*—Kidney-shaped.

*Margin.*—Bicrenated.

*Size of leaf.*—100 mm.

*Color of upper surface.*—Dark green, approximately 137 A.

*Color of zonation.*—Darker green, about 147 A.

*Tolerance of botrytis.*—Comparatively good, due to the relatively smooth surface of foliage.

General appearance and form:

*Internode length.*—20 mm.

*Branching pattern.*—1.2 branches per week.

*Height of foliage.*—26 cm, (in Jun., 16-week-old plants).

*Ploidy.*—Tetraploid.

It is claimed:

1. A new and distinct cultivar of geranium plant named Fisbravo, as illustrated and described.

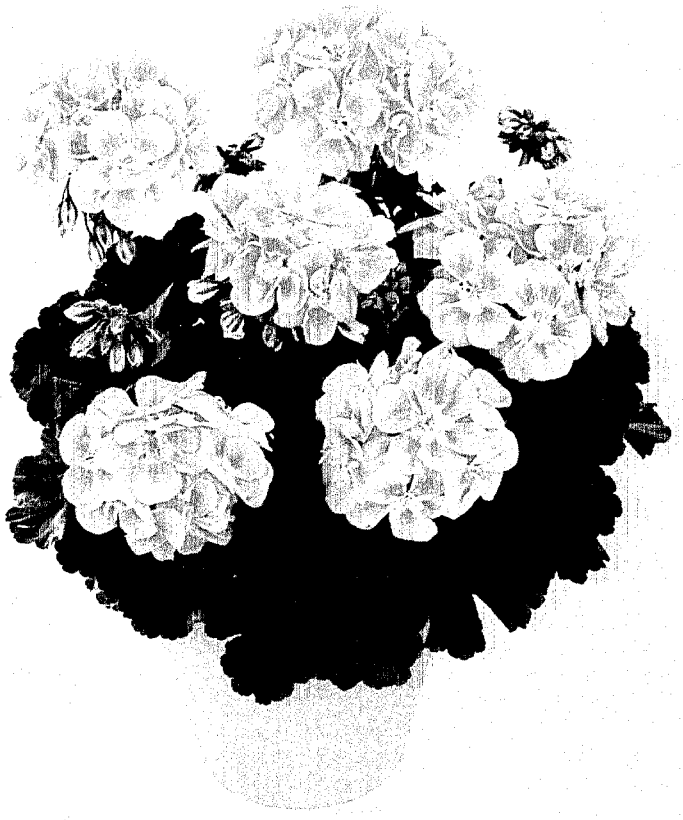

* * * * *